United States Patent
St. Laurent et al.

(10) Patent No.: US 9,149,488 B2
(45) Date of Patent: Oct. 6, 2015

(54) PHARMACEUTICAL COMPOSITION AND USE OF DIETHYL (2-CYANOETHYL)PHOSPHONATE

(71) Applicant: Olatec Industries LLC, Rye Brook, NY (US)

(72) Inventors: Joseph P. St. Laurent, Lakeville, MA (US); Gerald S. Jones, Norwood, MA (US); David M. Bresse, Middleboro, MA (US); Scott A. Goodrich, Stoughton, MA (US)

(73) Assignee: Olatec Industries LLC, New York, NY (US)

( * ) Notice: Subject to any disclaimer, the term of this patent is extended or adjusted under 35 U.S.C. 154(b) by 0 days.

(21) Appl. No.: 14/463,479

(22) Filed: Aug. 19, 2014

(65) Prior Publication Data

US 2015/0057252 A1  Feb. 26, 2015

Related U.S. Application Data (60) Provisional application No. 61/867,798, filed on Aug. 20, 2013.

(51) Int. Cl.
| | |
|---|---|
| *A61K 31/6615* | (2006.01) |
| *A61K 31/683* | (2006.01) |
| *A61K 9/00* | (2006.01) |
| *A61K 47/14* | (2006.01) |
| *A61K 47/32* | (2006.01) |
| *A61K 47/18* | (2006.01) |
| *A61K 47/10* | (2006.01) |
| *A61K 9/06* | (2006.01) |
| *A61K 47/34* | (2006.01) |
| *A61K 47/44* | (2006.01) |

(52) U.S. Cl.
CPC ............. *A61K 31/683* (2013.01); *A61K 9/0014* (2013.01); *A61K 9/06* (2013.01); *A61K 47/10* (2013.01); *A61K 47/14* (2013.01); *A61K 47/18* (2013.01); *A61K 47/32* (2013.01); *A61K 47/34* (2013.01); *A61K 47/44* (2013.01); *A61K 9/0053* (2013.01)

(58) Field of Classification Search
CPC .................................................. A61K 31/6615
See application file for complete search history.

(56) References Cited

U.S. PATENT DOCUMENTS

| | | | |
|---|---|---|---|
| 4,001,303 A | 1/1977 | Waldmann et al. | |
| 4,151,229 A | 4/1979 | Zondler | |
| 7,767,665 B2 * | 8/2010 | Kajino et al. | 514/226.5 |
| 8,476,316 B2 | 7/2013 | St. Laurent | |
| 2004/0242704 A1 | 12/2004 | Palczewski et al. | |
| 2010/0101651 A1 | 4/2010 | Wei et al. | |

FOREIGN PATENT DOCUMENTS

CN          101654279          3/2012

OTHER PUBLICATIONS

International Search Report for Application No. PCT/US2014/051735, mailed Dec. 3, 2014.

* cited by examiner

*Primary Examiner* — Samantha Shterengarts
(74) *Attorney, Agent, or Firm* — Perkins Coie LLP; Viola T. Kung (57) ABSTRACT

The present invention is directed to a pharmaceutical composition comprising a pharmaceutically acceptable carrier and diethyl(2-cyanoethyl)phosphonate, or a pharmaceutically acceptable salt thereof. The present invention is directed to a method for treating inflammation, inflammatory-related disorders, or pain, by administering diethyl(2-cyanoethyl)phosphonate, or a pharmaceutically acceptable salt or solvate thereof to a subject in need thereof.

15 Claims, 2 Drawing Sheets

PHARMACEUTICAL COMPOSITION AND USE OF DIETHYL (2-CYANOETHYL)PHOSPHONATE

This application claims priority to U.S. Provisional Application No. 61/867,798, filed Aug. 20, 2013; the content of which is incorporated herein by reference in its entirety.

FIELD OF THE INVENTION

The present invention relates to a pharmaceutical composition comprising a pharmaceutically acceptable carrier and diethyl(2-cyanoethyl)phosphonate, or its pharmaceutically acceptable salts. The present invention also relates to methods of using the compound for treating inflammation or inflammatory-related disorders and pain.

BACKGROUND OF THE INVENTION

Inflammation is a process by which microbes or tissue injury induce the release of cytokines and chemokines from various cell types producing increased blood vessel permeability, upregulation of endothelial receptors, and thus increased egress of various cells of the innate and adaptive immune system which enter surrounding tissue and grossly produce the classical picture of inflammation, i.e. redness, swelling, heat and pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, such as mediators and antigens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Based on the physical causes, pain can be divided into three types: nociceptive, neuropathic, and mix-type.

Nociceptive pain is the term for pain that is detected by nociceptors. Nociceptors are free nerve endings that terminate just below the skin, in tendons, in joints, and in internal organs. Nociceptive pain typically responds well to treatment with opioids and NSAIDs. There are several types of nociceptive pain: somatic pain, visceral pain, and cutaneous pain. Visceral pain comes from the internal organs. Deep somatic pain is initiated by stimulation of nociceptors in ligaments, tendons, bones, blood vessels, fasciae and muscles, and is dull, aching, poorly localized pain. Examples include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns. Nociceptive pain is usually short in duration and ends when the damage recovers. Examples of nociceptive pain include postoperative pain, sprains, bone fractures, burns, bumps, bruises, and inflammatory nociceptive pain. Inflammatory nociceptive pain is associated with tissue damage and the resulting inflammatory process.

Neuropathic pain is produced by damage to the neurons in the peripheral and central nervous systems and involves sensitization of these systems. Because the underlying etiologies are usually irreversible, most of neuropathic pain are chronic pain. Most people describe neuropathic pain as shooting, burning, tingling, lancinating, electric shock qualities, numbness, and persistent allodynia. The nomenclature of neuropathic pain is based on the site of initiating nervous system with the etiology; for examples, central post-stroke pain, diabetes peripheral neuropathy, post-herpetic (or post-shingles) neuralgia, terminal cancer pain, phantom limb pain.

Mix-type pain is featured by the coexistence of both nociceptive and neuropathic pain. For example, muscle pain trigger central or peripheral neuron sensitization leading to chronic low back pain, migraine, and myofacial pain.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

There is a need for a composition and a method for treating inflammation, inflammatory-related disorders, and pain. The composition should be economic and easy to manufacture, and the method should be effective and have no significant side effects.

SUMMARY OF THE INVENTION

The present invention is directed to a pharmaceutical composition comprising a pharmaceutically acceptable carrier and diethyl(2-cyanoethyl)phosphonate, or a pharmaceutically acceptable salt or solvate thereof. The compound is preferably at least 90% pure (w/w).

The present invention is also directed to a method for treating inflammation, inflammatory-related disorders, and pain. The method comprises the step of administering diethyl (2-cyanoethyl)phosphonate, or a pharmaceutically acceptable salt thereof to a subject in need thereof. The pharmaceutical composition comprising the active compound can be applied by any accepted mode of administration including topical, oral, and parenteral (such as intravenous, intramuscular, subcutaneous or rectal). Topical administration and oral administration are preferred.

DETAILED DESCRIPTION OF THE INVENTION

Definition

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$ (wherein X is $C_{1-4}$).

"Solvates," as used herein, are addition complexes in which the compound is combined with an acceptable co-solvent in some fixed proportion. Co-solvents include, but are not limited to, ethyl acetate, lauryl lactate, myristyl lactate, cetyl lactate, isopropyl myristate, ethanol, 1-propanol, isopropanol, 1-butanol, isobutanol, tert-butanol, acetone, methyl ethyl ketone, and diethyl ether.

Diethyl(2-cyanoethyl)phosphonate

The inventors have discovered diethyl(2-cyanoethyl)phosphonate or a pharmaceutically acceptably salt or solvate thereof, is effective for treating inflammation, inflammatory-related disorders, and pain.

diethyl (2-cyanoethyl)phosphonate

Diethyl(2-cyanoethyl)phosphonate, CAS Number 10123-62-3, also named (2-cyanoethyl)-phosphonic acid diethyl ester, or 3-(diethylphosphono)propionitrile, has a molecular weight of 191.16, is commercially available. Diethyl(2-cyanoethyl)phosphonate can be synthesized by various methods including: base-catalyzed condensation of diethyl phosphite with acrylonitrile (Tetrahedron Letters, 50(22), 2620-2623; 2009) and Arbuzov reaction of triethylphosphate and chloropropionitrile (Synthetic Communications, 25(21), 3443-55; 1995)].

Pharmaceutical Compositions

The present invention provides pharmaceutical compositions comprising one or more pharmaceutically acceptable carriers and an active compound of diethyl(2-cyanoethyl) phosphonate, or a pharmaceutically acceptable salt, or solvate thereof. The active compound or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation. The active compound used in the pharmaceutical composition in general is at least 90%, preferably 95%, or 98%, or 99% (w/w) pure.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in a dosage form such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cysteine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylenediaminetetraacetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of the active compound may comprise some inactive ingredients such as 1,3-butylene glycol, dihydroxyaluminum aminoacetate, disodium edetate, D-sorbitol, gelatin, kaolin, methylparaben, polysorbate 80, povidone (polyvinylpyrrolidone), propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In one embodiment, lauryl lactate (for example, at about 0.1-10%, or about 0.2-5%, or about 0.5-5%) is included in the topical gel formulation. Lauryl lactate is considered safe for topical administration. Lauryl lactate is qualified for human use within pharmaceutical and cosmetic products. Lauryl lactate when used in a topical formulation enhances the permeability of the compound. Preferably lauryl lactate is purified to achieve ≥90%, preferably ≥95% purity; the high purity mitigates the presence of hydrolytic and oxidative agents. In addition, DMSO at 0.1-20%, or 0.5-10% (w/w) in the formulation provides suitable solubility of the active compound.

In another embodiment, diethylene glycol monoethyl ether is included in the topical gel formulation.

Method of Use

Inflammation is a process and a state of tissue pathology resulting from activation and continuation of activity of the innate and acquired components of the immune system. The arachidonic acid cascade and cytokine production and action in cell to cell interactions are critical components of immune activation and response, which lead to inflammation. Arachidonic acid resides in many cell membranes. When arachidonic acids are cleaved from the membranes, it can produce many of the known eicosinoids including prostaglandins and leucotrienes, which are known pro-inflammatory entities.

The active compound is effective in inhibiting pro-inflammatory cytokine release when given orally to rat that were then challenged in vivo with lipopolysaccharide (e.g., IL-6, TNFα, IFNγ, MIP-2 and RANTES). The active compound is anti-inflammatory when applied topically in the mouse ear swelling model, in which the inflammation is induced by arachidonic acid. The present invention is directed to a method of treating inflammation and/or pain. Diethyl(2-cyanoethyl)phosphonate, can be used as is, or it can be administered in the form of a pharmaceutical composition that additionally contains a pharmaceutically acceptable carrier. The method comprises the steps of first identifying a subject suffering from inflammation and/or pain, and administering to the subject the active compound, in an amount effective to treat inflammation and/or pain. "An effective amount," as used herein, is the amount effective to treat a disease by ameliorating the pathological condition or reducing the symptoms of the disease.

In one embodiment, the method reduces or alleviates the symptoms associated with inflammation. The present invention provides a method to treat localized manifestations of inflammation characterized by acute or chronic swelling, pain, redness, increased temperature, or loss of function in some cases.

In another embodiment, the present invention provides a method to alleviate the symptoms of pain regardless of the cause of the pain. The general term "pain" treatable by the present method includes nociceptive, neuropathic, and mix-type. The present invention reduces pain of varying severity, i.e. mild, moderate and severe pain; acute and chronic pain. The present invention is effective in treating joint pain, muscle pain, tendon pain, burn pain, and pain caused by inflammation such as rheumatoid arthritis.

In one embodiment, the present invention is useful in treating inflammation and/or pain associated in a musculoskeletal system or on the skin. The highly innervated, musculoskeletal and skin systems have a high capacity for demonstration of pain. In addition, the musculoskeletal system has a high capacity for tissue swelling, and the skin has a high capacity for redness, swelling, and heat. In musculoskeletal and skin systems, the degree of tissue damage is frequently magnified out of proportion to the resulting inflammatory response. In the skin for example, merely firm stroking will cause release of the cytokines, IL-1 and TNF.

The present invention provides a method for treating inflammation and/or pain associated with inflammatory skeletal or muscular diseases or conditions. The method comprises the steps of identifying a subject in need thereof, and administering to the subject the active compound, in an amount effective to treat inflammation and/or pain. The skeletal or muscular diseases or conditions include musculoskeletal sprains, musculoskeletal strains, tendonopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epichondylitis (pitchers elbow) and trochanteric bursitis, temporomandibular joint syndrome, and fibromyalgia.

Skin is highly reactive to environmental stimuli and the epidermal component of keratinocytes is a very rich source of both arachidonic acid and pro-inflammatory cytokines of IL-1 and TNF. The skin dendritic cells, Langerhans cells, recognize and process antigens for further immune response of various lymphocytes and all of these cells are primarily regulated by cytokines through their specific cell surface receptors.

Diethyl(2-cyanoethyl)phosphonate, which is effective in inhibiting arachidonic acid induced inflammation and in inhibiting the release of pro-inflammatory cytokine, is effective to treat inflammation and/or pain associated with inflammatory skin diseases.

The present invention provides a method for treating inflammation and/or pain associated with inflammatory skin diseases such as psoriasis, acne, rosacea, and dermatitis, particularly contact dermatitis, and atopic dermatitis. The method comprises the steps of identifying a subject in need thereof, and administering to the subject the active compound, in an amount effective to treat inflammation and/or pain.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of the active compound delivered can vary; but are generally $1 \times 10^{-10}$-$1 \times 10^{-4}$ moles/liter, and preferably $1 \times 10^{-8}$-$1 \times 10^{-5}$ moles/liter.

In one embodiment, the composition is applied topically onto the affected area and rubbed into it. The composition is topically applied at least 1 or 2 times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administered orally to the subject. The dosage for oral administration is generally at least 0.1 mg/kg/day and less than 100 mg/kg/day. For example, the dosage for oral administration is 0.1-100 or 0.5-50 mg/kg/day, and preferably 1-20 or 1-10 mg/kg/day.

In one embodiment, the pharmaceutical composition is administered subcutaneously to the subject. The dosage for subcutaneous administration is generally 0.3-20, and preferably 0.3-3 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1

Gel Formulation 1

Table 1 exemplifies one gel formulation containing diethyl (2-cyanoethyl)phosphonate.

TABLE 1

|  | 5% Gel | 1% Gel |
|---|---|---|
| Active compound | 5.0% | 1.0% |
| Dow Corning Elastomer Blend EL-8050 ID | 61.4% | 63.4% |
| Labrafac Lipophile WL 1349 | 8.6% | 8.6% |
| Octisalate | 5.0% | 5.0% |
| Lauryl Lactate | 1.0% | 3.0% |
| Methyl Laurate | 5.0% | 7.0% |
| Dow Corning 556 Cosmetic Grade Fluid | 5.0% | 7.0% |
| Squalene | 2.0% | 2.0% |
| Sunflower Seed Oil | 2.0% | 2.0% |
| Diethylene Glycol Monoethyl Ether | 5.0% | 3.0% |
| Total | 100.0% | 100.0% |

Example 2

Gel Formulation 2

Table 2 exemplifies another gel formulation containing Diethyl(2-cyanoethyl)phosphonate.

TABLE 2

|  | 1-5% Gel |
|---|---|
| Active compound | 1.0-5.0% |
| Diethylene glycol monoethyl ether | 5.0% |
| Acrylates/C10-30 alkyl acrylate crosspolymer (CARBOPOL ® Ultrez 20 polymer) | 0.50% |
| Trolamine (tris(2-hydroxyethyl)amine) | 0.47% |
| Purified Water | 89.03-93.03% |
| Total | 100.0% |

Example 3

Anti-Inflammatory Activity of Active Compound by Topical Administration in Mice

Diethyl(2-cyanoethyl)phosphonate, was obtained from Sigma-Aldrich and used in this experiment.

The test compound, indomethacin (positive control), and vehicle (acetone:ethanol/1:1) were evaluated for anti-inflammatory activity in a topical arachidonic acid-induced ear swelling model in mice.

Male ICR mice weighing 22±2 g were used and randomly divided; the test compound and vehicle control had 10 mice, and indomethacin had 5 mice. Arachidonic Acid (0.5 mg in 20 μl of acetone:ethanol/1:1) was applied topically to the anterior and posterior surfaces of the right ear of each mice. Test substances (in vehicle) and vehicle, as listed in Table 1 were similarly applied 30 min before and 15 min after arachidonic acid application. The thickness of the right ear and the left ear was measured and the difference calculated as an indication of the inflammation in the right ear. Ear swelling was measured by a Dyer model micrometer gauge at 60 and 90 minutes after arachidonic acid application as an index of inflammation. Percent inhibition was calculated according to the formula: Ic−It/Ic×100, where Ic and It refers to increase of ear thickness (mm) in control and treated mice, respectively. An ANOVA was done, and if p<0.05, a Dunnett's t test was employed to calculate significant difference between vehicle control and test compound treated groups. A pairwise Student's t test was used to calculate differences between the indomethacin group and the control group. Significance is set at P<0.05 level. The results measured at 90 minutes after arachidonic acid application are summarized in Table 3.

TABLE 3

| Test Substance | Conc mM | Dosage | n | % Inhibition | P Value |
|---|---|---|---|---|---|
| Vehicle-acetone:ethanol (1:1) | 0 | 20 μL (0 mg/ear) applied twice | 10 | NA | NA |
| Indomethacin (Positive control) | 14 | 20 μL (0.1 mg/ear) applied twice | 5 | 58 | <0.001 |
| Diethyl (2-cyanoethyl) phosphonate in acetone:ethanol (1:1) | 375 | 20 μL (1.4 mg/ear) applied twice | 10 | 55 | <0.001 |

The topical administration of tested compound in mice resulted in 55% inhibition in the ear swelling induced by arachidonic acid, relative to that in the vehicle-treated group. The difference between test compound-treated mice and control mice was determined to be statistically significant.

Example 4

Anti-Inflammatory Activity of Active Compound by Intraperitoneal Administration in Mice The protocols of this experiment were similar to Example 3, except the following differences. Test substance diethyl(2- cyanoethyl)phosphonate was dissolved in PBS to generate 1, 3 and 10 mg/mL testing solutions. Vehicle (PBS) at 10 mL/kg and diethyl(2-cyanoethyl)phosphonate at 10 mL/kg (10, 30, and 100 mg/kg) were administered intraperitoneally at 1 hour, and again 15 minutes before arachidonic acid (0.5 mg/ear) challenge. The positive control dexamethasone was administered orally 3 hours before arachidonic acid.

An ANOVA was done, and if p<0.05, a Dunnett's t test was employed to calculate significant difference between vehicle control and treated groups. Significance is set at P<0.05 level. The results measured at 90 minutes after arachidonic acid application are summarized in Table 4.

An ANOVA was done, and if p<0.05, a Dunnett's t test was employed to calculate significant difference between vehicle control and test compound treated groups. A pairwise Student's t test was used to calculate differences between the dexamethasone group and the control group. Significance is set at P<0.05 level. The results measured at 90 minutes after arachidonic acid application are summarized in Table 4.

TABLE 4

| Test Substance | Dosage | n | % Inhibition | P Value |
|---|---|---|---|---|
| Vehicle-PBS | 0 | 10 | NA | NA |
| Dexamethasone (Positive control) | 0.3 mg/kg | 5 | 29 | 0.018 |
| Diethyl (2-cyanoethyl) phosphonate | 10 mg/kg | 10 | −8 | >0.05 |
| Diethyl (2-cyanoethyl) phosphonate | 30 mg/kg | 10 | 0 | >0.05 |
| Diethyl (2-cyanoethyl) phosphonate | 100 mg/kg | 10 | 34 | 0.017 |

(Dose volume for all groups was 10 mL/kg)

The intraperitoneal administration of tested compound at 100 mg/kg in mice resulted in 37% inhibition in the ear swelling induced by arachidonic acid, relative to that in the vehicle-control group. The difference between treated mice (at 100 mg/kg) and control mice was determined to be statistically significant. Intraperitoneal administration in the mouse is a good representation of the pharmacokinetic profile from other parenteral routes of administration (e.g., intravenous, subcutaneous, intramuscular). Therefore, the results indicate that parenteral administration of the test compound to a subject may be effective in reducing the symptoms of inflammation.

Example 5

Analgesic Activity of Active Compound by Oral Administration in Mice (Tail Flick Model)

Tail flick test is a test of the pain response in animals. Tail flick test is used in basic pain research and to measure the effectiveness of analgesics, by observing the tail flick reaction to heat in an animal. This test assesses the nociceptive response to a local pain stimulus, and the ability of a drug to inhibit this response.

Vehicle control (water) and test compound diethyl(2-cyanoethyl)phosphonate in water were administered by oral gavage to mice with a volume of 10 mL/kg, twice, at 60 and 15 minutes before the first tail flick measurement. The test compound was administered at a dosage of 10, 30, or 100 mg/kg in water. The positive control compound morphine was administered by subcutaneous injection at 8 mg/kg with a volume of 8 mL/kg, at 15 minutes before the first tail flick measurement. Each group had 10 mice.

The response of mice to heat stimulus was evaluated by measuring the time of tail-flick or tail-flick latency from 49° C. water bath. Briefly, the animal was placed in a restrainer with its tail hanging down. Approximately 2 inches of the tail was immersed in a beaker of water at 38±1° C. for about 30 seconds, and this was done twice to acclimate the animal to the procedure.

Subsequently, approximately 2 inches of the tail was immersed in a beaker of water at 49±1° C., at which point a timer was started. At the first sign of discomfort (whole body jerk, curvature or rapid movement of the tail), or at 30 second if the animal did not response, the timer was stopped, the latency time was recorded, and the tail was removed from the water.

Tail flick measurements were made 60, 80, 100, and 120 minutes post administration of the first dosage of test compound. An ANOVA was done, and if p<0.05, a Dunnett's t test was employed to calculate significant difference between vehicle control and test compound treated groups. A pairwise Student's t test was used to calculate differences between the morphine group and the control group. Results of tail flick response from each group are calculated as mean±SEM (standard error of mean). Analysis with p-values <0.05 is considered significant.

Figure 1:
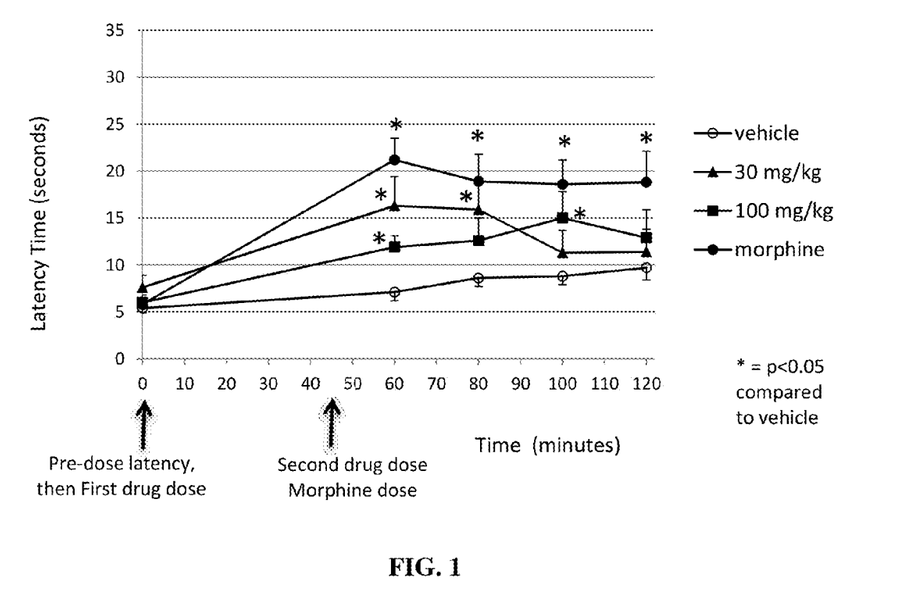
FIG. 1 shows the results of tail flick test of mice treated with vehicle (water, oral application), test compound (30 and 100 mg/kg in water, oral application) and morphine (subcutaneous application). The latency time of each group is calculated as mean±SEM and plotted against time, where * indicates p value <0.05 compared with vehicle-treated mice.

FIG. 1 shows the results of tail flick of mice treated with vehicle (water, oral application), test compound (30 and 100 mg/kg in water, oral application) and morphine (subcutaneous application). The latency time of each group is calculated as mean±SEM and plotted against time, where * indicates p value <0.05 compared with vehicle-treated mice.

As shown in FIG. 1, morphine-treated mice (subcutaneous injection) show statistically significant tail flick latency at all measured time points, when compared with vehicle-treated mice. Mice treated with test compound by oral administration at 30 mg/kg show statistically significant tail flick latency at 60 and 80 minutes, when compared with vehicle-treated mice. Mice treated with test compound at 100 mg/kg show statistically significant tail flick latency at 60 and 100 minutes, when compared with vehicle-treated mice. The above results provide evidence that test compound when administered orally, is effective in treating nociceptive pain in an animal.

Example 6

Analgesic Activity of Active Compound by Oral Administration in Mice (Formalin Model)

Formalin test is a model of continuous pain resulting from formalin-induced tissue injury. Nociceptive and inflammatory pain was induced by injection of a dilute formalin solution into the paw, resulting in nocifensive behavior including paw flinching. The formalin model encompasses inflammatory, neurogenic, and central mechanism of pain. The early phase of pain (from 0 to about 10 minutes) is due to nociceptive mechanism and the late phase of pain (from 10-40 minutes) is due to a combination of inflammatory pain and nociceptive mechanism. Pain behavior is assessed using manual paw licking measurements. The endpoints of the study are the number of paw licking events. (Hunskaar et al., *Pain*, 30:103-114, 1987; Li et al., *Molecular Pain*, 6:11, 2010)

Male CD-1 mice, about 34 g, were used in the study. Mice had free access to food and water, were maintained on a 12 hour: 12 hour light/dark schedule for the entire duration of the study, and housed in soft bedding five per cage.

Immediately prior to testing (at time 0), mice were restrained in a cloth and injected with 20 μL of a 5% formalin solution, subcutaneously into the dorsal surface of the left hind paw. Vehicle control (n=10, water) and test compound diethyl(2-cyanoethyl)phosphonate (n=9, in water) and were administered by oral gavage with a volume of 10 mL/kg to mice. The amounts of test compound were 10, 30, or 100 mg/kg per dose.

Positive control morphine was administered by subcutaneous injection at 4 mg/kg with a volume of 4 mL/kg to mice (n=10). The primary purpose of the positive control subcutaneous morphine group is for quality control, to confirm that the assay preforms consistently. The purpose of morphine is not to serve as a comparison with the test compound.

Morphine was subcutaneously administered once 15 minutes before formalin injection. The test compounds and vehicle control were orally administered twice (BID), at 60 and 15 minutes before formalin injection at time zero.

Following formalin injection, animals were placed in individual cages, and manually observed for 60 minutes. The licking events were recorded in five minute intervals continuously for a total of 60 minutes.

Test compound at 10 or 30 mg/kg did not show a statically significant difference from control.

Figure 2:
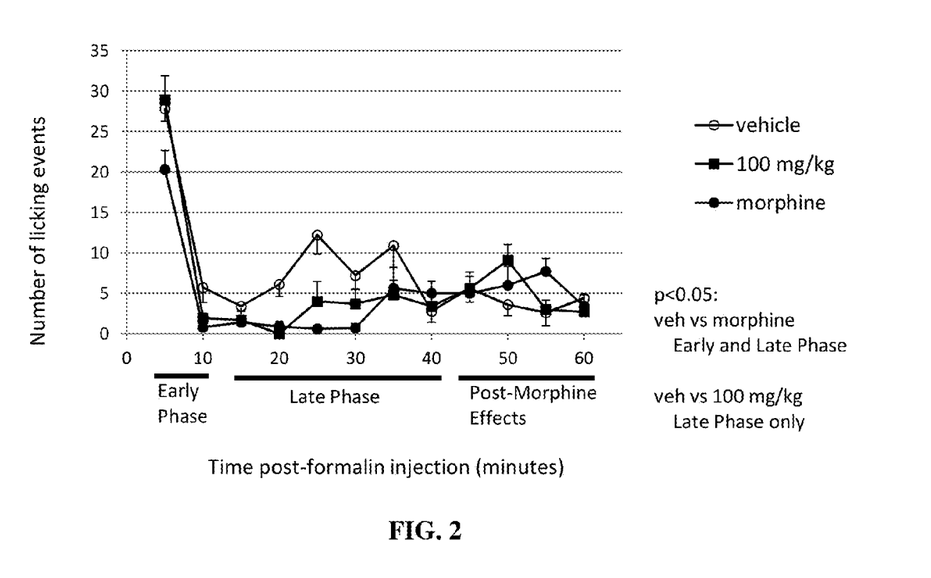
FIG. 2 shows the results of formalin test of mice treated with vehicle (oral application), test compound (oral application at 100 mg/kg) and morphine (subcutaneous application). The number of licking events per 5 minute interval is calculated as mean±SEM and plotted against time after formalin injection.

The number of licking events at different time points post formalin injection of vehicle control, morphine-treated (100 mg/kg), and test compound-treated mice were plotted in 5 minute intervals in FIG. 2.

The number of licking events per minute was calculated between 0-10 minutes and 10-40 minutes for vehicle, positive control, and test compound. An ANOVA was done, and if p<0.05, a Dunnett's t test was employed to calculate significant difference between vehicle control and test compound treated groups. A pairwise Student's t test was used to calculate differences between the morphine group and the control group. Significance is set at P<0.05 level. The results are summarized in Table 5.

TABLE 5

| Test Substance | Dosage | Licks per min (Between 0-10 min) | P Value | Licks per min (Between 10-40 min) | P Value |
|---|---|---|---|---|---|
| Vehicle (water) | 0 oral | 3.3 | NA | 1.4 | NA |
| Morphine (Positive control) | 4 mg/kg subcutaneous | 2.1 | 0.0026 | 0.47 | 0.00084 |
| Diethyl (2-cyanoethyl) phosphonate | 100 mg/kg oral | 3.1 | >0.05 | 0.59 | 0.006 |

Morphine at 4 mg/kg by subcutaneous administration had statistically significant (p<0.05) reductions in the number of events in early phase between 0 and 10 minute, and in late phase between 10 and 40 minutes, but the efficacy did not last after 40 minutes due to clearance of the drug.

At 100 mg/kg BID, test compound demonstrated efficacy by showing a statistically significant (p<0.05) reduction in the number of events in the late phase between 10 and 40 minutes, but it did not last after 40 minutes. There was no statistically significant difference between test compound and control in early phase between 0 and 10 minutes. The results indicate that test compound is effective in treating inflammatory nociceptive pain.

Example 7

Analgesic Activity of Active Compound by Topical Administration in Mice (Formalin Model)

The animals and the treatment protocol were similar to those described in Example 6, except the following.

The test compound diethyl(2-cyanoethyl)phosphonate (375 mM in vehicle, n=16) and vehicle control (acetone:ethanol 1:1, n=16) were administered topically by submerging the mouse left hind paw in the respective solution for about 30 seconds. The paw was then withdrawn and wiped with tissue to avoid excess dermal drying.

Positive control morphine was administered by subcutaneous injection at 4 mg/kg with a volume of 4 mL/kg to mice (n=16).

Morphine was subcutaneously administered once 15 minutes before formalin injection. The test compounds and vehicle control were topically administered twice (BID), at 90 and 15 minutes before formalin injection.

Following formalin injection, animals were placed in individual cages, and manually observed for 60 minutes. The licking events were recorded in five minute intervals continuously for a total of 40 minutes.

Figure 3:
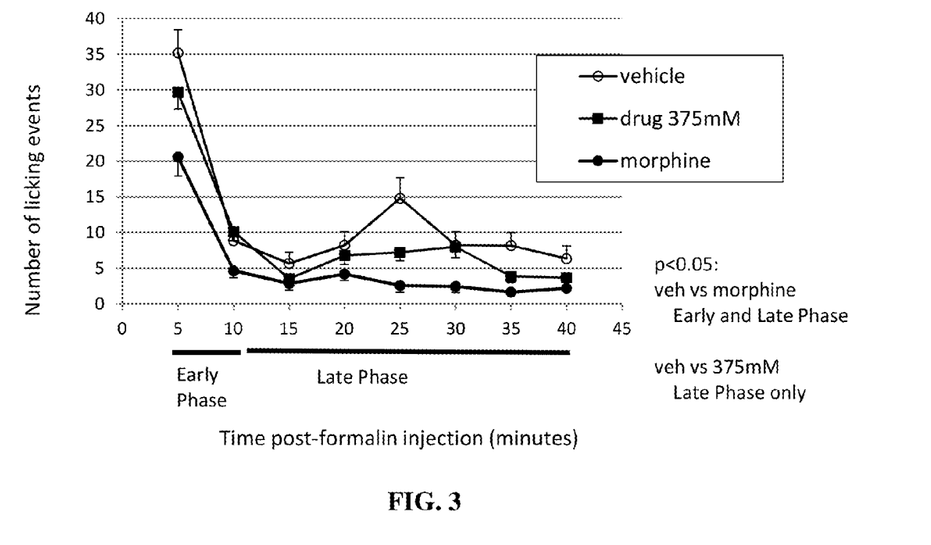
FIG. 3 shows the results of formalin test of mice treated with vehicle (topical application), test compound (topical application of at 375 mM) and morphine (subcutaneous application). The number of licking events per 5 minute interval is calculated mean±SEM and plotted against time after formalin injection.

The number of licking events at different time points post formalin injection of vehicle control, morphine-treated, and test compound-treated mice were plotted in FIG. 3.

The number of licking events per minute was calculated between 0-10 minutes and 10-40 minutes for vehicle, positive control, and test compound. A two-sample t-test was done to compare the vehicle group with the test compound group. Significance is set at P<0.05 level. The same statistics were done comparing the vehicle group with the positive control group. The results are summarized in Table 6.

TABLE 6

| Test Substance | Dosage | Licks per min (Between 0-10 min) | P Value | Licks per min (Between 10-40 min) | P Value |
|---|---|---|---|---|---|
| Vehicle (acetone:ethanol) | 0 Topical | 4.4 | NA | 1.7 | NA |
| Morphine (Positive control) | 4 mg/kg subcutaneous | 2.5 | 0.000411 | 0.53 | 0.000163 |
| Diethyl (2-cyanoethyl) phosphonate | 375 mM topical | 4.0 | >0.05 | 1.1 | 0.018 |

Morphine at 4 mg/kg by subcutaneous administration had statistically significant (p<0.05) reductions in the number of events in early phase between 0 and 10 minute, and in late phase between 10 and 40 minutes, At 375 mM, test compound demonstrated efficacy by showing a statistically significant (p<0.05) reduction in the number of events in the late phase between 10 and 40 minutes. There was no statistically significant difference between test compound and control in early phase between 0 and 10 minutes. The topical application of test compound alone without injection of formalin resulted in a negligible number of paw licking events.

The results indicate that test compound is effective in treating inflammatory nociceptive pain by topical application.

Example 8

Analgesic Activity of Active Compound in Chronic Constriction Injury Model (Prophetic Example)

Peripheral nerve lesions may generate a syndrome comprising, in addition to spontaneous pain, exaggerated responses to light touch (tactile allodynia). Chronic constriction injury model is a neuropathic pain model.

Male Sprague Dawley rats weighing 180±20 g are used. Under pentobarbital (50 mg/kg, 5 ml/kg, i.p.) anesthesia, the sciatic nerve is exposed at mid-thigh level. Four ligatures (4-0 chromic gut), about 1 mm apart, are loosely tied around the nerve. The animals are then housed individually in cages with soft bedding for 7 days before testing. Constriction of the sciatic nerve produces nerve injury and unilateral neuropathic pain.

On the day of experiments, the animals have no access to food overnight before testing. The rats are placed under inverted plexiglass cages on a wire mesh rack and allowed to acclimate for 20 to 30 minutes. Mechanic allodynia is evaluated by the Chaplan up/down method using von Frey filaments to the plantar surface of the left hind paw. See Chaplan, et al. J. Neuroscience Methods, 53: 55-63, 1994.

Rats are pre-selected for experimentation only if the pain threshold 7-14 days after nerve ligation (pre-treatment) is reduced by 10 grams of force relative to the response of the individual paw before nerve ligation (pre-ligation), namely, with clear presence of allodynia.

The active compound diethyl(2-cyanoethyl)phosphonate is prepared in the gel formulation according to Example 2.

Active compound in gel formulation (1-5%), active compound in 1% Tween 80, morphine (positive control, p.o., 20 mg/kg), topical vehicle (gel formulation without an active compound), and oral vehicle (1% Tween 80 in water) are evaluated.

Test substance or vehicle is either administered orally (30-100 mg/kg) or topically (1-5% gel formulation) to the plantar surface of the left hind paw. The mechanical allodynia test is performed 30 min before (pre-treatment) and 1 and 3 hours after a single dose of test substance or vehicle (post treatment). Paw withdraw thresholds of control and tested compound are measured.

Example 9

Treatment of Knee Pain by Topical Administration (Prophetic Example)

Objectives: To investigate the efficacy of the active compound in a topical gel formulation in human patients with mild to severe knee pain associated with osteoarthritis following temporary cessation of standard NSAID therapy. The focus of this study is on the symptoms caused by painful arthritis. The clinical trial is utilizing osteoarthritis of the knee as a well-established paradigm for other musculoskeletal disorders.

Topical Formulation: The gel formulations containing the active compound diethyl(2-cyanoethyl)phosphonate at 1% and 5% (Example 2) are used in this example. Placebo contains the same gel without the active compound.

Methodology: A randomized, double-blind, placebo controlled, parallel treatment multicenter clinical activity study.

Patients with painful osteoarthritis of the knee, controlled by a stable dose of standard NSAID therapy for at least 2 months, discontinue use of the NSAIDs for a 7-day washout period.

Patients are then randomized in a 1:1:1 ratio (1% active gel, 5% active gel, placebo). A total of up to 150 patients are enrolled.

The active gel or placebo is applied to the affected knee 3 times a day for 12 weeks for a total of 252 treatments given every 4-6 hours while awake.

Patients are treated for 12 weeks and followed up for a further 4 weeks. NSAIDs may be restarted after the Week 12 visit.

Criteria for Evaluation:

Safety:

Adverse Events (AEs) throughout the study.

Physical examination at enrollment (−7 days, start of NSAID washout period), Baseline (Day 1, start of treatment), Week 12 and Week 16.

Vital signs at enrollment (−7 days, start of NSAID washout period), Baseline (Day 1, start of treatment) and Weeks 2, 4, 6, 12 and 16.

Clinical laboratory measurements at Baseline (Day 1), Week 4, 8, 12 and 16.

Clinical Activity:

The primary clinical activity parameters are the measurement of pain in the target joint, as quantified by the Visual Analog Scale (VAS) and the Western Ontario and McMaster University (WOMAC) Index pain subscale. The effect of treatment on swelling, tenderness and inflammation of the knee is recorded, also the time to reduction or eradication of pain after treatment is recorded.

Study Endpoints:

The primary clinical activity endpoint is:

Change from Baseline (Day 1) to Week 12 in WOMAC functional disability index pain subscale (Scale 0-20)

The secondary clinical activity endpoints are:

Change from Baseline (Day 1) to Week 12 in WOMAC functional disability index subscales:

Stiffness (Scale 0-8).

Physical function (Scale 0-68).

Change from Baseline (Day 1) to Week 12 in VAS pain score (0-100).

Change from Baseline (Day 1) to Week 2 in VAS pain score (0-100).

Change in investigator evaluation of swelling, tenderness and inflammation between Baseline (Day 1) and Weeks 4 and 12 after the first application on Day 1.

Time to reduction or eradication of pain subsequent to each topical application of active gel or placebo gel.

Use of rescue medication (APAP).

Example 10

Treatment of Knee Pain by Oral Administration (Prophetic Example)

The design and protocols of this experiment are similar to those described in Example 9, except the active compounds and placebo are applied by an oral route.

Oral Formulation: Tablet formulations containing 10, 100, or 1000 mg of the active compound diethyl(2-cyanoethyl)phosphonate are used in this example. Placebo has the same tablet formulation without the active compound.

Methodology:

Patients are then randomized in a 1:1:1:1 ratio (10 mg: 100 mg: 1000 mg: placebo). A total of up to 200 patients are enrolled.

The active tablet or placebo is administered orally to each patient two times a day for 12 weeks for a total of 168 treatments given every 12 hours while awake. Patients are treated for 12 weeks and followed up for a further 4 weeks.

Criteria for evaluation are the same as those described in Example 9.

It is to be understood that the foregoing describes preferred embodiments of the present invention and that modifications may be made therein without departing from the scope of the present invention as set forth in the claims.

What is claimed is:

1. A pharmaceutical composition comprising a pharmaceutically acceptable carrier and a compound of diethyl(2-cyanoethyl)phosphonate, or a pharmaceutically acceptable salt thereof.

2. The pharmaceutical composition according to claim 1, wherein the compound has at least 90% (w/w) purity, and the composition is in a topical form of gels, creams, lotions, ointments, or patches.

3. The pharmaceutical composition according to claim 2, wherein the pharmaceutically acceptable carrier is an emollient selected from the group consisting of: lauryl lactate, diethylene glycol monoethyl ether, caprylic/capric triglyceride, octisalate, silicone fluid, squalene, and sunflower oil.

4. The pharmaceutical composition according to claim 2, wherein the pharmaceutically acceptable carrier is a permeation enhancer selected from the group consisting of lactate esters and diethylene glycol monoethyl ether.

5. The pharmaceutical composition according to claim 4, further comprising acrylates/C10-30 alkyl and tris(2-hydroxyethyl)amine.

6. The pharmaceutical composition according to claim 1, wherein the compound has at least 90% (w/w) purity, and the composition is in an oral form of tablets, capsules, or syrups.

7. A method of treating inflammation or pain, comprising the steps of:

identifying a subject suffering from inflammation or pain, and administering to the subject the pharmaceutical composition of claim 1, in an amount effective to treat inflammation or pain.

8. The method according to claim 7, wherein said method reduces or alleviates the symptoms of localized manifestations of inflammation characterized by acute or chronic swelling, pain, or redness.

9. The method according to claim 7, wherein said inflammation and/or pain is associated with a skeletal or muscular disease or condition selected from the group consisting of: musculoskeletal sprains, musculoskeletal strains, tendonopathy, peripheral radiculopathy, osteoarthritis, degenerative joint disease, juvenile arthritis, gout, ankylosing spondylitis, psoriatic arthritis, system lupus erythematosus, costochondritis, tendonitis, bursitis, temporomandibular joint syndrome, and fibromyalgia.

10. The method according to claim 7, wherein said inflammation and/or pain is associated with joints, ligaments, tendons, bone, muscles, or fascia.

11. The method according to claim 7, wherein said inflammation and/or pain is associated with an inflammatory skin disease or disorder of dermatitis or psoriasis.

12. The method according to claim 11, wherein said dermatitis is atopic dermatitis or contact dermatitis.

13. The method according to claim 7, wherein said compound is administered by systemic administration.

14. The method according to claim 7, wherein said compound is administered by topical administration.

15. The method according to claim 7, wherein said compound is administered by oral administration.

\* \* \* \* \*